United States Patent [19]

Heldebrant

[11] Patent Number: 4,490,361
[45] Date of Patent: Dec. 25, 1984

[54] VIRUS INACTIVATING HEAT TREATMENT OF PLASMA FRACTIONS

[75] Inventor: Charles M. Heldebrant, Arcadia, Calif.

[73] Assignee: Alpha Therapeutic Corporation, Los Angeles, Calif.

[21] Appl. No.: 557,665

[22] Filed: Dec. 2, 1983

[51] Int. Cl.³ .............................................. A61K 35/16
[52] U.S. Cl. ...................................... 424/101; 424/95
[58] Field of Search ................................. 424/95, 101

[56] References Cited

U.S. PATENT DOCUMENTS

| | | |
|---|---|---|
| 2,405,216 | 8/1946 | Josh . |
| 4,404,187 | 9/1983 | Schwinn et al. . |
| 4,405,603 | 9/1983 | Schwinn et al. . |
| 4,456,590 | 6/1984 | Rubenstein ......................... 424/101 |

Primary Examiner—Sam Rosen
Attorney, Agent, or Firm—Christie, Parker & Hale

[57] ABSTRACT

A process is provided for heat treating a protein powder that includes mixing the powder into an organic liquid to form a suspension and heating the suspension for a selected time at a selected temperature. Such heat treatment inactiviates any virus associated with the protein while not substantially impairing the biological activity of the protein.

24 Claims, No Drawings

VIRUS INACTIVATING HEAT TREATMENT OF PLASMA FRACTIONS

FIELD OF THE INVENTION

The process provided in accordance with this invention relates to heat treating a lyophilized protein powder suspended in an organic liquid to thereby inactivate any virus associated with the protein while not substantially impairing the biological activity of the protein.

BACKGROUND OF THE INVENTION

Various biologic products are produced from biological materials obtained from human and non-human sources. These biologic products can be administered to humans as a medical treatment. Thus, it is desirable and, in fact, imperative that the biologic products be free from infectious components, for example, active viral agents.

A major source for such biologic products is human blood plasma. For example, such biologic products can include various fractions of protein materials separated from human plasma, such as albumin, antithrombin III, fibrinogen, factor VIII (anti-hemophilic factor [AHF]), and the prothrombin complex, i.e., factor IX, together with factors II, VII and X.

Inactivation of viral agents, e.g., hepatitis B virus and/or non-A, non-B hepatitis virus, can be accomplished by treating the plasma before the fractions are separated, or the fractions can be treated after separation.

Various treatments to inactivate infectious agents in separated fractions have been used in the past. Such treatments can, for example, include the use of solutions containing bleach, alkali, and/or acids. However, using such solutions is highly deleterious to the labile protein fractions and can destroy their biological activity and, thus, their usefulness.

Other treatments that have been used in the past are exposure of separate protein fractions to ultraviolet radiation or β-propiolactone.

Treatments are also known which use heat to inactivate infectious agents contained in plasma and in protein fractions separated from such plasma. For example, aqueous solutions of Antithrombin III, Factor VIII (AHF), albumin, Plasma Protein Fraction (PPF), and Factor IX have been heated to temperatures from 60° C. to 100° C. to inactivate viral components. Also plasma has been subjected to heat.

Alternatively, various protein fractions have been heated in the dry state, for example, as a powder, to deactivate viral components.

Heating aqueous solutions of protein fractions, or heating the protein fraction in its dry state, can result in the material losing a greater portion of its biological activity than desired. Furthermore, heating such materials in the dry state may not provide heating that is as uniform as desired.

Thus, there is a need in the art for a process that is relatively simple and inexpensive, that provides even heating to the protein fraction being sterilized, and that does not substantially reduce the biological activity of the material being treated.

SUMMARY OF THE INVENTION

A process is provided in accordance with this invention for inactivating a virus associated with a biological material, e.g., protein fractions separated from blood plasma. The biological material is initially provided in the form of a dry powder. The dry biological material powder is mixed into an organic liquid to thereby form a suspension of the powder in the liquid. The suspension is heated to a selected temperature for a selected period of time to thereby inactivate any virus associated with the biological material while substantially maintaining the biological activity of the biological material. The suspended biological material is then separated from the organic solvent, and the separated biological material is dried and recovered.

The dried recovered biological material is then further processed into an appropriate physiologically acceptable formulation for administration to a patient.

DETAILED DESCRIPTION

In accordance with practice of the process of this invention, biological materials, e.g., protein materials, are heated to inactivate any virus which may be associated therewith.

Such protein materials can, for example, be one or more protein fractions that have been separated from human blood plasma. Protein fractions that can be heat-treated in accordance with practice of this invention include, but are not limited to, albumin, antithrombin III, fibrinogen, factor VIII (anti-hemophilic factor [AHF]), and prothrombin complex proteins, i.e., factor IX, factor II, factor VII, and factor X. Other protein materials can also be heat-treated to inactivate viruses associated therewith in accordance with this invention.

Separation of protein fractions, such as those mentioned above, from human plasma is well known in the art. For example, methods for separating protein fractions from plasma are disclosed in U.S. Pat. No. 2,390,074 to E J. Cohn and in E. J. Cohn, L. E. Strong, W. L. Hughes, D. J. Mulford, J. N. Ashworth, M. Melin and H. L. Taylor, *Separation Into Fractions of Protein and Lipoprotein Components*, J. Am. Chem. Soc. 68 (1946), p. 459–475. Both U.S. Pat. No. 2,390,074 and the above-referenced article are incorporated herein by this reference.

The protein fraction to be sterilized or "heat-treated" in accordance with the process of this invention is dried, e.g., lyophilized, to form a protein powder. The powder is then mixed into an inert organic liquid. The protein powder does not dissolve in organic liquids useful in practice of this invention, but instead the powder is dispersed in particle form in the liquid to thereby form an organic liquid/protein powder suspension. Organic liquids that are useful in practice of principles of this invention are alkane liquids, such as hexane, the like; ketones, such as acetone, diethyl ketone, and the like; and perfluorochemicals, such as perfluorotripropylamine, for example. Other similar organic liquids are also thought to be useful, so long as the liquid forms a suspension with the protein powder being treated.

The organic liquid/protein powder suspension is then heated to a temperature from about 60° C. to about 100° C. for a selected period of time to thereby inactivate or destroy any virus associated with the protein. The selected time can, for example, be from about 5 minutes to about 30 hours, depending on the temperature. Longer time periods are used when the suspension is heated to relatively lower temperatures, and shorter time periods are used when the suspension is heated to relatively higher temperatures. For example, when the suspension is heated to about 60° C., the time period for heating is preferably not less than about 10 hours and more preferably is not less than about 20 hours. Alternatively, when the suspension is heated to between about 98° C. and 100° C., the time period for heating is preferably not less than about 30 minutes, but it can be substantially less than about 10 hours.

At the conclusion of the heating step, the heat-treated organic liquid/protein powder suspension is filtered or otherwise processed to recover the heat-treated protein powder, and the organic liquid can be discarded. The protein powder is then air-dried for a selected time, and the dried powder is further processed to provide it in the form of a sterilized biologic product sufficiently free from residual organic liquid to form a physiologically acceptable formulation ready for administration to a patient.

Factor VIII, i.e., anti-hemophilic factor (AHF), can be separated from human plasma for heat treatment in accordance with practice of this invention as outlined in the procedure of Examples 1–2 below. Prothrombin complex proteins (PTC) can be separated from human plasma for heat treatment in accordance with this invention as outlined in Example 3 below. It should be noted that AHF and PTC, as well as other proteins, can be provided for heat treatment in accordance with this invention by any of a variety of methods well known in the art.

EXAMPLE 1

Separation of Anti-Hemophilic Factor (AHF) From Human Plasma (Polyethylene Glycol Process)

AHF is separated from human plasma that has been collected and tested according to procedures approved by the U.S. Food and Drug Administration. The plasma is initially frozen at a temperature of about −20° C. The frozen plasma is then thawed at 0° C. to +5° C. and pooled. The cryoprecipitate, which forms during the thawing process, is then removed by centrifugation and rinsed with either cold distilled water or a 0.02 M (Molar) Tris (Tris-hydroxymethyl-aminomethane)-HCl buffer to wash off any excess plasma that adheres to its surface. The rinsed cryoprecipitate is then suspended in a 0.02 M Tris-HCl buffer at a neutral pH for about 30–60 minutes to provide an extracted cryoprecipitate. The Tris-AHF suspension is then adsorbed with aluminum hydroxide (Al[OH]$_3$) gel for at least 10 minutes, after which the Al(OH)$_3$ gel is removed by centrifugation. The centrifugate, i.e., the Al(OH)$_3$ filtrate, is then clarified through a membrane or cartridge filter. The filtered AHF solution is stabilized with dilute sodium citrate solution, and then polyethylene glycol (PEG) is added to a final concentration of about 4.5%, followed by gentle mixing for about 30 minutes. The precipitate formed is removed by centrifugation and discarded. Additional PEG is added to the AHF-PEG centrifugate to a final concentration of about 15% to form an AHF precipitate. The AHF precipitate suspension is gently mixed for about 30 minutes, and the precipitate is then collected by centrifugation. The resulting AHF precipitate is suspended in about 2.5 M glycine-citrate solution containing not more than about 1% PEG. The suspension is mixed until a homogeneous mixture is formed, after which it is centrifuged to recover the final AHF precipitate.

The AHF precipitate is then dissolved in a dilute Tris-citrated saline solution, and the pH is adjusted to about neutral. The final AHF solution is then filtered through a sterilized bacteria-retentive membrane or cartridge filter to form a sterile bulk solution. The sterile bulk solution is then lyophilized, and the lyophilized AHF powder is collected for heat treatment in accordance with practice of this invention.

EXAMPLE 2

Separation of Anti-Hemophilic Factor (AHF) From Human Plasma (CG Process)

A cryoprecipitate is recovered and rinsed using the same steps that are set forth in Example 1 above. The rinsed cryoprecipitate is suspended in about a 0.02 M Tris-HCl buffer at about room temperature. The pH is adjusted to about 6.4, and the temperature of the suspension is lowered. The suspension is then centrifuged, and the solid contaminants and precipitate are discarded. The centrifugate is then adjusted to about a neutral pH with dilute NaOH, and the temperature of the centrifugate is raised to about room temperature. The centrifugate is then adsorbed with Al(OH)$_3$ gel, after which the Al(OH)$_3$ gel is removed by centrifugation and discarded. The centrifugate is then clarified through a membrane or cartridge filter. To the clarified centrifugate is added about 2.0 M sodium citrate solution to a final concentration of about 0.02 M, and the pH is adjusted to about neutral. The AHF solution is then filtered through previously sterilized bacteria-retentive membranes or cartridge filters to form a sterile bulk solution. The sterile bulk solution is lyophilized, and the lyophilized AHF powder is collected for heat treatment in accordance with practice of principles of this invention.

EXAMPLE 3

Separation of Prothrombin Complex Proteins From Human Plasma

Prothrombin complex proteins (PTC) are separated from human plasma that has been collected and tested according to procedures approved by the U.S. Food and Drug Administration. The plasma is initially frozen at a temperature of about −20° C. The plasma is then thawed at 0° C. to +5° C. to allow cryoprecipitation to occur. The resulting plasma-cryoprecipitate mixture is pooled and centrifuged to remove the cryoprecipitate. The pooled AHF-poor plasma is then weighed, brought to 0° C. to +5° C., and electrodialyzed to reduce the plasma sodium concentration from its original value to between 85 and 105 mM. The dialyzed AHF-poor plasma is then adjusted to about a neutral pH by the addition of acetic acid.

The prothrombin complex factors contained in the pH adjusted AHF-poor plasma are adsorbed by the addition of regenerated DEAE (diethyl aminoethyl) cellulose. The DEAE cellulose and the plasma are mixed approximately 30 minutes, and the DEAE cellulose is then collected by centrifugation. The DEAE cellulose-adsorbed prothrombin complex is washed with a buffer comprising about 0.03 M sodium phosphate and about 0.03 M sodium citrate at a pH of about 6.8. The wash is discarded.

The washed DEAE cellulose-adsorbed prothrombin complex is then removed from the centrifuge and suspended in a wash buffer. The resulting suspension is then poured into a column, and the eluate from the column is discarded. The column containing the DEAE cellulose is then washed with a wash buffer, and this wash is also discarded. The prothrombin complex factors are then eluted by washing the column with an eluting buffer comprising 0.03 M sodium phosphate, 0.03 M sodium citrate, and 0.2 M sodium chloride at a pH of about 6.8. The eluate is collected, and the prothrombin complex fractions are pooled and collected in a bulk solution. Appropriate tests of the collected prothrombin complex fractions are made, and, after the pH of the bulk solution is adjusted to about neutral, the solution is filtered through a sterile bacteria-retentive cartridge or membrane to thereby form a bulk solution of filtered prothrombin complex (PTC). The bulk solution of filtered PTC is then lyophilized, and the lyophilized PTC powder is collected for heat treatment in accordance with practice of principles of this invention.

In an exemplary embodiment of practice of principles of this invention of heat-treating AHF, provided in accordance with either Examples 1 or 2 above, the AHF is dispersed, i.e., suspended, in an organic liquid, such as hexane, heptane, acetone, or perfluorotripropylamine or the like. The AHF suspension is then heated to about 60° C. to 100° C. for between 5 minutes and about 30 hours. After the heating step is concluded, the suspension is filtered, and the AHF powder is recovered. The sterile AHF powder is then air-dried to remove residual organic liquid.

The air-dried heat-treated AHF powder is then dissolved in a glucose solution. (The amount of glucose solution used is preferably about 20±10 liters (l) of such glucose solution per kilogram (kg) of heat-treated AHF powder.) The pH of the glucose/AHF solution is adjusted to 7.0±0.1 with a dilute sodium hydroxide solution or dilute hydrochloric acid solution. The final AHF solution is then centrifuged and filtered through previously sterilized bacteria-retentive membrane or cartridge filters to remove undissolved (denatured) protein material.

The AHF solution is then sampled for testing and is filled into sterilized vials and lyophilized. The lyophilized AHF powder is, at this point, ready to be dissolved in sterile water to form an appropriate physiologically acceptable solution or formulation for administration to a patient.

A series of experiments were conducted to determine various properties of protein fractions that are heat-treated in accordance with practice of this invention.

EXAMPLE 4

Heat Treatment of AHF Powder in Acetone 0.5 grams (gm) of lyophilized AHF powder from lot Al-1150 separated from human plasma in accordance with Example 2 were dissolved in 20 milliliters (ml) of acetone and stirred for 10 minutes with a stirring bar to form a suspension of AHF in acetone. The suspension was sealed in a vial and heated to 60° C. for 10 hours. Following the completion of the heating step, the suspension was filtered through Whatman No. 1 filter paper to recover the heated AHF powder. The acetone was discarded. The AHF powder was then air-dried for 12–18 hours and then dissolved in 20 ml of distilled water and the solution filtered to remove insoluble material.

A sample of the resulting heat-treated AHF solution was then analyzed for AHF activity and compared to the AHF activity of a control sample of AHF from the same lot that had not been heat-treated.

The heat-treated AHF had 70.7% of the AHF activity of the control.

EXAMPLE 5

Heat Treatment of AHF Powder in Hexane 0.5 grams of lyophilized AHF powder from lot Al-1150 was processed in accordance with the procedure of Example 4 above, except that hexane was substituted for acetone.

The heat-treated AHF had 62.4% of the AHF activity of the control.

EXAMPLE 6

Heat Treatment of AHF Powder in Perfluorotripropylamine 0.5 grams of lyophilized AHF powder from lot Al-1150 was processed in accordance with the procedure of Example 4 above, except that perfluorotripropylamine was substituted for acetone. The heat-treated AHF had 59.7% of the AHF activity of the control.

EXAMPLE 7

Heat Treatment of AHF Powder in Heptane for Various Time Periods

Lyophilized AHF powder from lot Al-1881 provided in accordance with Example 2 was dissolved in heptane and stirred for 10 minutes with a stirring bar to form a suspension of AHF in heptane. The suspension was sealed in a vial and boiled at 98° C. Samples were taken of the heated powder at 5, 10, 15, 20, and 30 minute intervals. At the conclusion of the heating period, each such powder-heptane suspension sample was filtered through Whatman No. 1 filter paper to recover the heated AHF powder. The heptane was discarded. Each sample was air-dried for 12–18 hours and then dissolved in distilled water and filtered to remove insoluble material. A sample of each of the resulting heat-treated AHF solutions were analyzed for activity and compared to the activity of a control sample of AHF prepared from the same lot that had not been heat treated. The AHF activity of the control was 2.4 units/ml, while the AHF activities of the heat-treated samples were as follows:

The sample taken at 5 minutes—1.38 units/ml;
The sample taken at 10 minutes—1.58 units/ml;
The sample taken at 15 minutes—1.56 units/ml;
The sample taken at 20 minutes—1.58 units/ml;
The sample taken at 30 minutes—1.35 units/ml.

The heat-treated samples as a group had an AHF activity of 62.8% of the control sample.

EXAMPLE 8

Heat Treatment of Protein Fraction Powders in Heptane

Two samples of protein taken from each of three stages of the method of Example 1 and a sample of AHF prepared by the method of Example 2 were heat-treated in accordance with the process of this invention. The protein samples taken from the materials being processed in accordance with Example 1 comprise two samples of the cryoprecipitate, two samples of the extracted cryoprecipitate, and two samples of the Al-(OH)$_3$ filtrate. The samples of cryoprecipitate and extracted cryoprecipitate were lyophilized and heat-treated in hexane. The two Al(OH)$_3$ filtrate samples and the two AHF samples provided in accordance with Example 2 were lyophilized and heat-treated in heptane.

The lyophilized powder of each sample was dispersed in its respective organic liquid in a vial and stirred for 10 minutes with a stirring bar. Each sample vial was sealed and heated to 60° C. for 10 hours. Following the completion of the heating step, each sample was filtered through Whatman No. 1 filter paper to recover its respective protein powder. The powder comprising each such sample was air-dried for 12–18 hours, and then each dry powder sample was dissolved in a 1.0% glucose solution in a vial. The volume of 1% glucose used is 20±10 liters per kilogram of heat-treated powder. The pH was adjusted to 7±0.1 with a dilute sodium hydroxide solution or dilute hydrochloric acid solution as appropriate. Each final protein solution was then filtered through a sterilized bacteria-retentive membrane or cartridge filter. The final protein powder solution was then sampled for sterility and filled into previously sterilized vials. The protein powder solution in each such vial was then frozen and lyophilized under sterile conditions. After lyophilization of the protein solutions, the lyophilized product was analyzed for yield, and the results are shown in Table I.

TABLE I

| Sample | *Yield (%) | |
|---|---|---|
| Cryoprecipitate | Run 1, | 6.24 |
| | Run 2, | 4.72 |
| Extracted Cryoprecipitate | Run 1, | 2.58 |
| | Run 2, | 5.68 |
| Al(OH)₃ Filtrate | Run 1, | 2.22 |
| | Run 2, | 1.00 |
| Final Bulk C(G) AHF | Run 1, | 7.00 |

*"Yield (%)" is the total AHF activity in the lyophilized final product as a percentage of the total AHF activity in the original plasma used to prepare the product.

EXAMPLE 9

Heat Treatment of AHF Prepared in Accordance With Example 2

Three separate 300-gram samples of cryoprecipitate were processed in accordance with Example 2. The lyophilized powder from each of the three runs was dispersed in heptane and stirred for 10 minutes with a stirring bar. Each sample was sealed in a vial and heated at 60° C. for 10 hours. Following completion of the heating, the AHF powder/heptane suspension was filtered through Whatman No. 1 filter paper to recover the AHF powder. The powder was air-dried for 12–18 hours, and then it was dissolved in distilled water, filtered, and lyophilized.

The properties of the heat-treated lyophilized powder and a corresponding control comprising lyophilized AHF concentrate that was not heat-treated were compared. The results of the comparison are shown in Table II.

TABLE II

| Run # | Units of AHF Activity Per Vial | *% Total Protein | Specific Activity AHF Units/mg Protein | **Yield (%) |
|---|---|---|---|---|
| 1 Heat-Treated AHF | 564 | 3.79 | 0.595 | 14.90 |
| 1 Control | 627 | 3.02 | 0.623 | 18.72 |
| 2 Heat-Treated AHF | 355 | 3.78 | 0.376 | 13.14 |
| 2 Control | 394 | 3.86 | 0.408 | 16.42 |
| 3 Heat-Treated AHF | 504 | 2.65 | 0.761 | 12.19 |
| 3 Control | 482 | 2.62 | 0.736 | 14.65 |

*"% Total Protein" is the concentration of protein in each vial, reconstituted with the recommended amount of sterile water, expressed as grams of protein per 100 ml of reconstituted solution.
**"Yield (%)" is the total AHF activity in the lyophilized final product as a percentage of the total AHF activity of the original plasma used to prepare the product.

EXAMPLE 10

Heat Treatment of AHF Prepared in Accordance With Example 2 (Pilot Scale)

One kilogram of cryoprecipitate provided in accordance with Example 2 was dispersed in heptane and stirred for 10 minutes with a stirring bar. The powder/heptane suspension was sealed in a vial and heated at 60° C. for 10 hours. Following completion of the heating, the powder/heptane suspension was filtered through Whatman No. 1 filter paper to recover the AHF powder. The powder was air-dried for 12–18 hours and then dissolved in distilled water and filtered to remove suspended material and was poured into vials and lyophilized. Properties of the heat-treated AHF concentrate provided in accordance with this example are shown in TABLE III.

TABLE III

| AHF Concentrate Property | Heat-treated AHF |
|---|---|
| Specific Activity | 0.648 AHF units/mg protein |
| Anti A isoagglutinnin | 1:64 |
| Anti B isoagglutinnin | 1:64 |
| % Total Protein* | 4.32 |
| pH | 6.96 |
| Activity | 280 units/vial |
| Moisture | 1.27% |
| Yield (%)** | 14.7 |

*"% Total Protein" is the concentration of protein in each vial, reconstituted with the recommended amount of sterile water, expressed as grams of protein per 100 ml of reconstituted solution.
**"Yield (%)" is the total AHF activity in the lyophilized final product as a percentage of the total AHF activity of the original plasma used to prepare the product.

EXAMPLE 11

Heat Treatment of the Protein Fraction Designated "Peg Precipitate" Prepared in Accordance With Example 1

A 40-gram sample of protein material at the PEG precipitate stage being prepared in accordance with Example 1 was dissolved in 0.02 M sodium citrate and the pH adjusted to about 7. The solution was filtered and lyophilized. The lyophilized powder was dispersed in heptane and heat-treated at 60° C. for 10 hours. The heat-treated suspension was filtered to retain the protein powder, and the retained powder was air-dried for 12–18 hours and then dissolved or reconstituted in 1.0% glucose solution at a pH of 7.0±0.5. The resulting solution was sterile-filtered through a bacteria-retentive membrane filter, filled into vials, and lyophilized under sterile conditions.

The properties of the heat-treated product were compared to a control lot of AHF (lot No. A3-2260) provided in accordance with the process of Example 1. The control lot was not subjected to heat treatment techniques provided in accordance with this invention. Table IV includes this comparison.

TABLE IV

| AHF Specification | Heat-treated AHF | Control (Lot A3-2260) |
|---|---|---|
| Specific Activity (AHF units/mg protein) | 1.46 | 1.77 |
| Anti A isoagglutinnun | 1:64 | 1:128 |
| Anti B isoagglutinnun | 1:64 | 1:64 |
| pH | 6.64 | 6.87 |
| Moisture | 0.5% | 0.95% |
| Yield (%)* | 16.5% | 18.7% |

*"Yield (%)" is the total AHF activity in the lyophilized final product as a percentage of the total AHF activity of the original plasma used to prepare the product.

EXAMPLE 12

Heat Treatment of Prothrombin Complex Proteins (PTC)

A lyophilized prothrombin complex powder produced in accordance with Example 3 (lot No. 72-059-SL) was dispersed in heptane and the resulting suspension was filled into vials. The vials, each of which contained the same amount of the suspension, were heated at 60° C. for 10 hours. The potencies of three factors, namely factor II, factor IX and factor X were assayed after heat treatment and compared with the results of a control of the same lot that had not been heat treated. The results are shown in TABLE V.

TABLE V

| Factors | Heat Treated | Control (non-Heat Treated) |
|---|---|---|
| Factor IX | 474 units/vial | 579 units/vial |
| Factor II | 385 units/vial | 423 units/vial |
| Factor X | 243 units/vial | 254 units/vial |

EXAMPLE 13

Hepatitis B Virus Activity in Heat-Treated Protein Fractions (Chimpanzee Study)

262 grams of cryoprecipitate was processed by the process of Example 1 to the PEG precipitate stage. The PEG precipitate was dissolved in a 0.02 M sodium citrate solution, and the pH was adjusted to about 7. The solution was filtered and then poured into vials, with each vial containing about 250 units of AHF activity. Infectious heptatis B virus, at a dose of 500 chimpanzee infectious doses (CID), or 10,000 CID, was added to each vial. The material in each vial was lyophilized to form a powder. The powder from each of the vials was dispersed in heptane and individually heat-treated. One group of vials was treated at a temperature of about 60° C. for 20 hours (62° C.±2° C.). A second group of vials was treated at a temperature of 98° C. for 30 minutes. Material, i.e., the protein powder, in a control group of vials was not heated. After the heat treatment step, the protein powder/heptane suspensions that were heat-treated i.e., the suspensions heated at 60° C. and also those heated at 98° C., were filtered and air-dried for 12-18 hours to provide a heat-treated protein powder.

Protein powder samples of the 60° heat-treated material, the 98° C. heat-treated material and the control (non-heat-treated) material were then reconstituted with 10 ml of sterile water for injection of each such sample into a susceptible chimpanzee to thereby determine whether the hepatitis B virus in such samples was still infectious.

Seven samples were provided by this procedure for injection into seven chimpanzees: two samples (vials) of the 500 CID material heated in heptane at a temperature of about 60° C. for 20 hours; two samples (vials) of the 10,000 CID material heated in heptane at a temperature of about 60° C. for 20 hours; one sample (vial) of the 500 CID material heated in heptane at a temperature of 98° C. for 30 minutes; one sample (vial) of the 10,000 CID material heated in heptane at a temperature of 98° C. for 30 minutes; and one 500 CID control sample (unheated).

The entire contents of each test sample vial was injected intravenously into a different one of the chimpanzees, and the chimpanzees were observed for the following six-month period. Blood samples were taken from each of the chimpanzees on a weekly basis during the six-month observation period, and the samples were evaluated to determine whether the chimpanzees had contracted hepatitis B. If the blood sample was negative for hepatitis B surface antigen (HBsAg), the chimpanzee had not contracted hepatitis B, while if the blood sample was positive for HBsAg, the chimpanzee had contracted hepatitis B.

The results of the six-month chimpanzee test are shown in Table VI.

TABLE VI

| Chimpanzee No. | Dose | Heat-Treatment Method/Time | Hepatitis B Surface Antigen (HBsAg) Status |
|---|---|---|---|
| 419 | 500 CID | None (Control) | HBsAg positive 11 weeks after injection |
| 400 | 500 CID | 62° C. ± 2° C. for 20 hrs. | Negative |
| 392 | 500 CID | 62° C. ± 2° C. for 20 hrs. | Negative |
| 382 | 10,000 CID | 62° C. ± 2° C. for 20 hrs. | Negative |
| 417 | 10,000 CID | 62° C. ± 2° C. for 20 hrs. | HBsAg Positive 8 weeks after injection |
| 398 | 500 CID | 98° C. for 30 min. | HBsAg Positive 9 weeks after injection |
| 380 | 10,000 CID | 98° C. for 30 min. | HBsAg Positive 8 weeks after injection |

The results of the six-month chimpanzee study demonstrate that heat-treating the protein material of Example 13 at a temperature of about 60° (in this case 62° C.±2° C.) for 20 hours inactivates at least 500 CID of hepatitis B virus, as shown by the negative tests on chimpanzees Nos. 392 and 400. The results also show that heating the protein material of Example 13 at a temperature of about 60° C. for 20 hours inactivates a dose of hepatitis B virus between 500 and 10,000 CID, as shown by the one negative chimpanzee (No. 382, injected with the 10,000 CID material) and the one positive chimpanzee (No. 417, injected with the 10,000 CID material). The results further demonstrate that heat-treating the protein material of Example 13 at a temperature of 98° C. for 30 minutes does not inactivate 500 CID of hepatitis B virus, as shown by the positive tests on animals Nos. 398 and 380.

While heating at 98° C. for 30 minutes does not completely inactivate a 500 CID dose of hepatitis B virus, such heating would inactivate a lesser indeterminate dose of hepatitis B virus.

It was also found during the six-month observation period that the control animal (chimpanzee No. 419) developed non-A, non-B hepatitis, while none of the other test animals developed such non-A, non-B hepatitis. It was therefore concluded that heat-treating of protein materials in accordance with Example 13 inactivates an indeterminate dose of an unidentified non-A, non-B hepatitis virus.

EXAMPLE 14

Heat Treatment of the Protein Fraction Designated "Peg Precipitate" Prepared in Accordance With Example 1 (Human Study)

A production lot of human plasma was processed by the procedure outlined in Example 1 to the PEG precipitate stage. The PEG precipitate paste was then collected and divided into portions; one-third being processed by the continuing method of Example 1, and constituting a control lot (A3-2590) of AHF, and two-thirds being reconstituted in a 0.02 M sodium citrate solution. The pH of the reconstituted paste was adjusted to about 7, and the solution was sterile-filtered and lyophilized.

The protein powder, i.e., the AHF, produced by being reconstituted in 0.02 sodium citrate solution, was split into two lots. The first such AHF lot (A9-2590B) was dispersed in heptane, filled into vials which were sealed, and then heated at 61° C. +1° C. for 20 hours and 10 minutes. Following completion of the heating, the AHF powder/heptane suspension was filtered through Whatman No. 1 filter paper to recover the AHF powder. The AHF powder was then air-dried for 12-18 hours, and the air-dried powder was dissolved in 1% glucose solution at a pH of about 7. The resulting solution was sterile-filtered, filled into vials, and lyophilized.

The second AHF lot (A9-2590A) was dispersed in heptane, and the AHF powder/heptane dispersion was heated at 98° C. for 30 minutes. Following the completion of the heating step, the AHF powder/heptane suspension was filtered through Whatman No. 1 filter paper to recover the AHF powder. The powder was air-dried for 12-18 hours, and the air-dried powder was dissolved in a 1% glucose solution, and the pH was adjusted to about 7. The resulting solution was sterile-filtered, filled into vials and lyophilized.

Samples of the control lot and of both heat-treated lots were analyzed. The results of this example are given in Table VII.

TABLE VII

| Test | Lot No. A3-2590 | Lot No. A9-2590B | Lot No. A9-2590A |
| --- | --- | --- | --- |
| Factor VIII Activity (units/vial) | 830 | 570 | 810 |
| Protein (grams/100 ml) | 2.17 | 2.29 | 2.32 |
| Specific Activity (AHF units/milligram protein) | 1.54 | 1.00 | 1.40 |
| pH | 6.7 | 6.8 | 6.8 |
| Moisture (%) | 0.33 | 0.96 | 0.77 |
| Isoagglutinnins (titer) | | | |
| Anti-A | 1:64 | 1:128 | 1:128 |
| Anti-B | 1:32 | 1:128 | 1:128 |
| Heptane (micrograms/vial) | 0 | 0.321 | Not Determined |

AHF from the control lot (A3-2590) and from each of the lots heat-treated in accordance with Example 14 (A9-2590A and A9-2590B) were reconstituted with sterile water to provide vials containing at least 20 units of AHF per ml of final solution.

Seven human patients were injected with reconstituted AHF from lot A3-2590 (control) on a given date and, either one week earlier or one week later, depending on the patient, were injected with reconstituted heat-treated AHF from lot A9-2590A.

Six different human patients were injected with reconstituted AHF from lot A3-2590 (control) on a given date and, either about one week earlier or one week later, depending on the patient, were injected with reconstituted heat treated AHF from lot A9-2590B.

From 3 to 6 vials of reconstituted AHF was administered in each separate "injection".

There were no adverse reactions resulting from administration of the reconstituted lots A3-2590 (control) or A9-2590B. One patient experienced a mild headache after infusion of reconstituted AHF from lot A9-2590A, but this was a transitory effect. No treatment was required, and, after 10 minutes, the patient no longer felt any discomfort. All six of the other patients who received injections of reconstituted AHF from lot A9-2590A were symptom-free.

During these studies, there were no significant differences noted as to the effect on the patient of administering reconstituted AHF from the control lot (A3-2590) when compared to the effect on the patient of administering reconstituted AHF from either lot A9-2590A or lot A9-2590B. There were also no statistically significant differences between the control lot (A3-2590) and either of the two heat-treated lots (A9-2590A and A9-2590B) with respect to the AHF in-vivo recovery or the AHF in vivo half life, indicating that the preparations had equal biological efficacy.

Although the above-described exemplary embodiments of the process of this invention for heat-treating a protein material is described in terms of AHF and prothrombin complex proteins produced in accordance with Examples 1-3, AHF and prothrombin complex proteins produced by other methods can also be heat-treated in accordance with this process. Also, as mentioned above, protein materials other than AHF and prothrombin complex proteins can be heat-treated in accordance with practice of principles of this process to provide a sterile biological material that has substantially maintained its biological activity.

The above descriptions of exemplary embodiments of the process for inactivating a virus associated with a biological material are for illustrative purposes. Because of variations, which will be apparent to those skilled in the art, the present invention is not intended to be limited to the particular embodiments described above. The scope of the invention is defined in the following claims.

What is claimed is:

1. A process for inactivating a virus associated with a biologically active material, the process comprising the steps of:
   (a) providing the biological material in the form of a dry powder;
   (b) mixing the dry biological material powder into an organic liquid to thereby form a suspension of the powder in the liquid;
   (c) heating the suspension formed in step (b) to a selected temperature for a selected period of time to thereby inactivate any virus associated with the biological material, while substantially maintaining the biological activity of the biological material; and thereafter (d) separating the suspended biological material from the organic liquid and recovering the separated biological material.

2. A process according to claim 1 wherein the suspension is heated to a selected temperature in the range of from about 60° C. to about 100° C.

3. A process according to claim 2 wherein the selected period of time is from about 5 minutes to about 30 hours.

4. A process according to claim 1 wherein the organic liquid is selected from the group consisting of alkanes, ketones, and perfluorochemicals.

5. A process according to claim 1 wherein the organic liquid is heptane.

6. A process according to claim 1 wherein the organic liquid is hexane.

7. A process according to claim 1 wherein the organic liquid is acetone.

8. A process according to claim 1 wherein the organic liquid is perfluorotripropylamine.

9. A process according to claim 1 wherein the selected temperature is about 60° C., and the selected time period is from about 10 hours to about 30 hours.

10. A process according to claim 1 wherein the suspension is heated to a selected temperature in the range of from about 95° C. to about 100° C., and the selected time period is from about 30 minutes to about 10 hours.

11. A process according to claim 1 wherein the biological material comprises at least one protein fraction separated from human plasma.

12. A process according to claim 1 wherein the biological material is selected from the group consisting of albumin, antithrombin III, fibrinogen, Factor VIII, the prothrombin complex, and mixtures thereof.

13. A process according to claim 1 wherein the biological material includes Factor VIII separated from human plasma.

14. A process according to claim 1 wherein the virus is the hepatitis B virus.

15. A process for inactivating a virus associated with a plasma fraction containing Factor VIII, the process comprising the steps of:
(a) providing the plasma fraction in the form of a dry powder;
(b) mixing the dry plasma fraction powder into an organic liquid to thereby form a suspension of the powder in the liquid;
(c) heating the suspension formed in step (b) to a temperature in the range of from about 60° C. to about 100° C. for a selected period of time to thereby inactivate any virus associated with the plasma fraction, while substantially maintaining the biological activity of the Factor VIII contained in the plasma fraction; and thereafter
(d) separating the suspended plasma fraction from the organic liquid and recovering the separated plasma fraction.

16. A process according to claim 15 wherein the selected period of time is from about 5 minutes to about 30 hours.

17. A process according to claim 15 wherein the organic liquid is selected from the group consisting of alkanes, ketones, and perfluorochemicals.

18. A process according to claim 16 wherein the organic liquid is heptane.

19. A process according to claim 15 wherein the organic liquid is hexane.

20. A process according to claim 15 wherein the organic liquid is acetone.

21. A process according to claim 15 wherein the organic liquid is perfluorotripropylamine.

22. A process according to claim 15 wherein the suspension is heated to about 60° C., and the selected time period is from about 10 hours to about 30 hours.

23. A process according to claim 15 wherein the suspension is heated to a temperature in the range of from about 95° C. to about 100° C., and the selected time period is from about 30 minutes to about 10 hours.

24. A process according to claim 15 wherein the virus is the hepatitis B virus.

* * * * *

UNITED STATES PATENT AND TRADEMARK OFFICE
CERTIFICATE OF CORRECTION

PATENT NO. : 4,490,361

DATED : December 25, 1984

INVENTOR(S) : Charles M. Heldebrant

It is certified that error appears in the above-identified patent and that said Letters Patent is hereby corrected as shown below:

Column 2, line 52 after "hexane," add -- and --; column 6, line 38 change "were" to -- was --; column 8, line 50 change "Peg Precipitate" to -- "PEG Precipitate" --; column 9, lines 8, 9 change "isoagglutinnun" to -- isoagglutinin -- (both occurrences); column 11, line 8 change "Peg Precipitate" to -- "PEG Precipitate" --; column 12, line 35 change "is" to -- are --; column 14, line 25 change "16" to -- 15 --.

Signed and Sealed this

Twenty-first Day of May 1985

[SEAL]

Attest:

DONALD J. QUIGG

Attesting Officer   Acting Commissioner of Patents and Trademarks